US00PP16241P2

(12) United States Plant Patent
Mowrey et al.

(10) Patent No.: US PP16,241 P2
(45) Date of Patent: Feb. 7, 2006

(54) STRAWBERRY PLANT NAMED 'DRISCOLL PEARL'

(50) Latin Name: *Fragaria×ananassa*
Varietal Denomination: Driscoll Pearl

(75) Inventors: Bruce D. Mowrey, Watsonville, CA (US); Kristie L. Gilford, Dover, FL (US); Larry T. Kodama, Watsonville, CA (US); JoAnne Cross, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 98 days.

(21) Appl. No.: 10/957,401

(22) Filed: Oct. 1, 2004

(51) Int. Cl.
*A01H 5/00* (2006.01)

(52) U.S. Cl. ..... Plt./209

(58) Field of Classification Search ..... Plt./209
See application file for complete search history.

*Primary Examiner*—Anne Marie Grunberg
*Assistant Examiner*—Annette H Para
(74) *Attorney, Agent, or Firm*—Jones Day

(57) ABSTRACT

This invention relates to a new and distinct variety of strawberry named 'Driscoll Pearl.' The variety is similar to the varieties 'San Juan' and 'Driscoll Lanai.' The variety is distinguished from 'San Juan' and 'Driscoll Lanai,' in particular, by its longer petiole length, longer fruiting truss length, upright growth habit, strong sweetness of fruit, and highly susceptibility to powdery mildew.

5 Drawing Sheets

1. Latin name of the genus and species of the plant claimed: The variety is botanically identified as *Fragaria× ananassa.*

1.1 Variety denomination: The strawberry variety denomination is 'Driscoll Pearl'.

2. BACKGROUND OF THE INVENTION

The new variety originated as a result of a controlled cross between the strawberry plants 'San Juan' (U.S. Pant Pat. No. PP12,899) and '88E94' (unpatented) in an ongoing breeding program, and was discovered as a seedling in Monterey County, Calif. in 2000. The original seedling of the new cultivar was asexually propagated by stolons in a Nursery in Shasta County, Calif. Propagules were transplanted to a controlled breeding plot in Monterey County, Calif., where the variety was identified and selected for further evaluation. 'Driscoll Pearl' was subsequently asexually propagated and underwent further testing in Monterey County, Calif. for four years. This propagation and testing has demonstrated that the combination of traits disclosed herein which characterize the new variety are fixed and retained true to type through successive generations of asexual reproduction.

3. SUMMARY OF THE INVENTION

The present invention relates to a new and distinct variety of strawberry named 'Driscoll Pearl.' The variety is botanically identified as *Fragaria×ananassa.* The new variety is distinguished from other varieties by a number of characteristics as set forth in Tables 1–4.

4. COMPARISON TO SIMILAR VARIETIES

The varieties which we believe to be similar to 'Driscoll Pearl' from those known to us are 'San Juan' and 'Driscoll Lanai' (U.S. Plant Pat. No. PP15,145). There are several characteristics of the new variety that are different from, or not possessed by 'San Juan' and 'Driscoll Lanai'. For example, the new variety has a longer petiole length, a longer fruiting truss length, an upright growth habit, strong sweetness of fruit, and is highly susceptible to powdery mildew.

The paternal parent, 88E94, was not available for side by side comparison with 'Driscoll Pearl'. 'Driscoll Pearl' differs from 88E94 by having superior fruit size and shelf-life, greater plant vigor, dark red fruit color compared to 88E94s oranged red. 'Driscoll Pearl' also differs from 88E94 by being partially everbearing while 88E94 was fully everbearing. 'Driscoll Pearl' is distinguished from its maternal parent 'San Juan' as indicated in Tables 1–4.

5. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

6. DESCRIPTION OF THE NEW VARIETY

Figure 1:
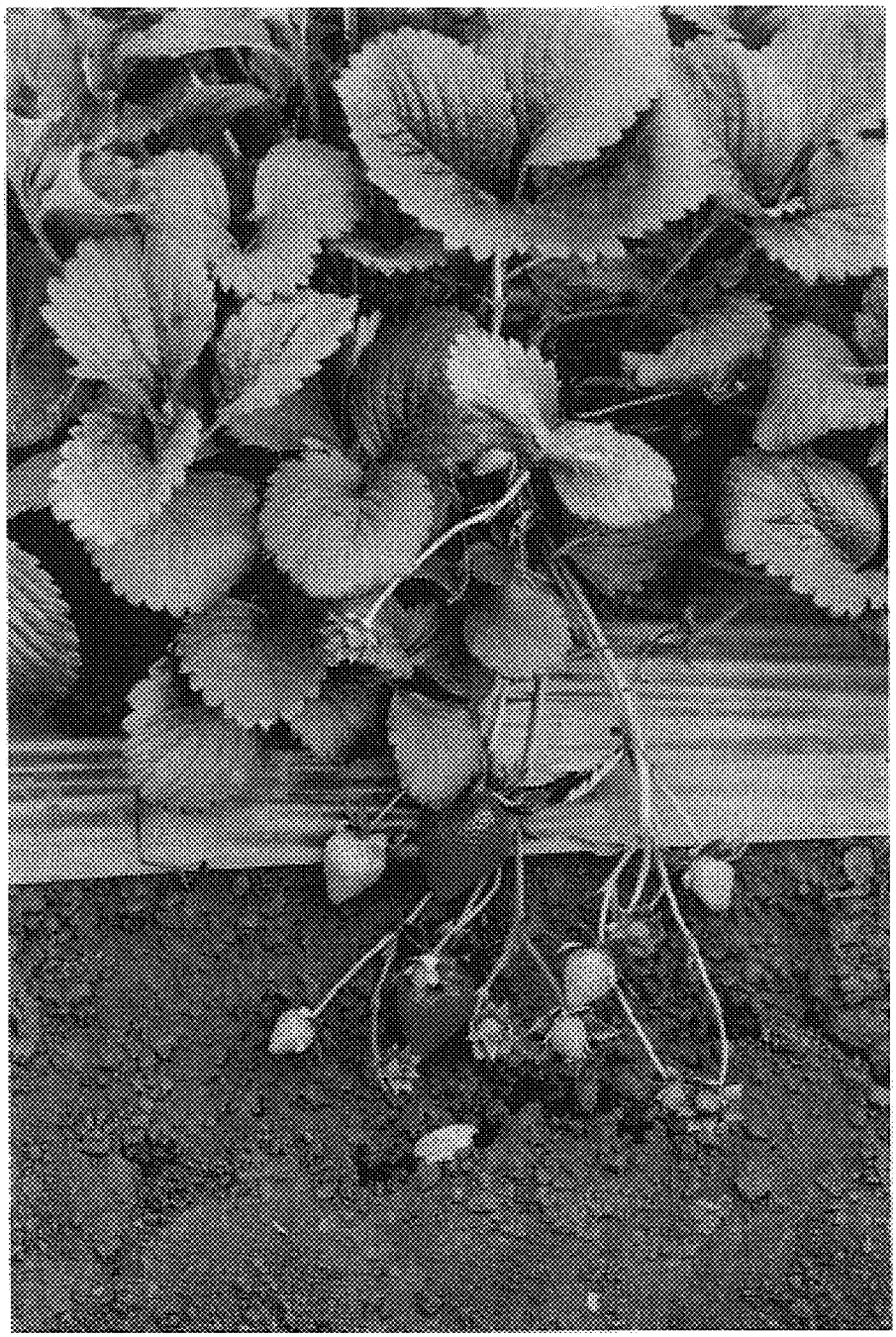
FIG. 1 shows the whole the plant.
Figure 2:
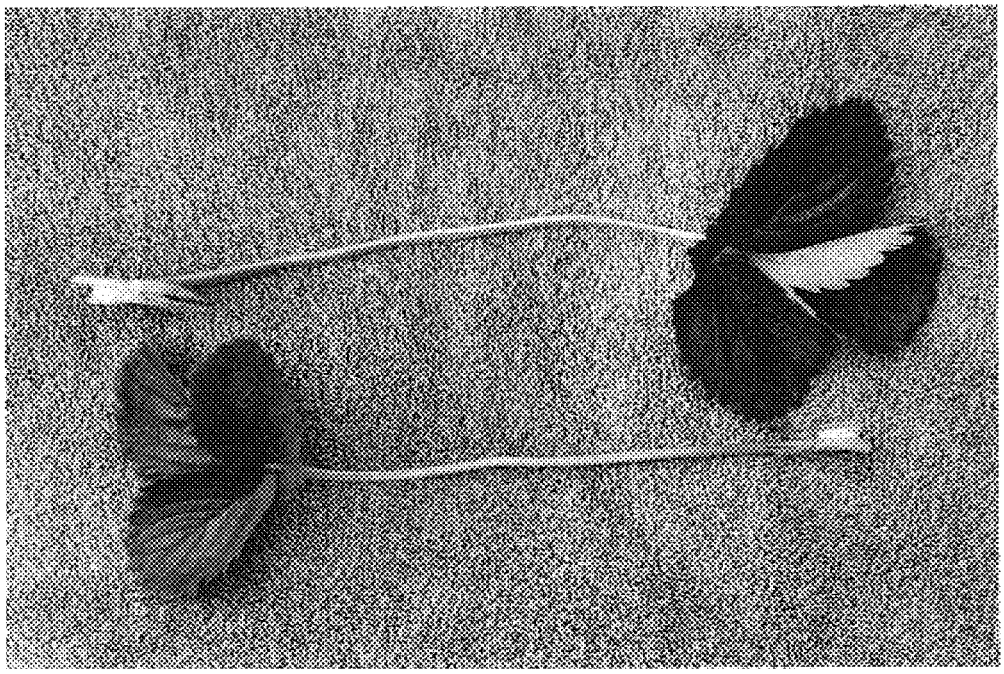
FIG. 2 shows the upper side of the leaves of the plant.
Figure 3:
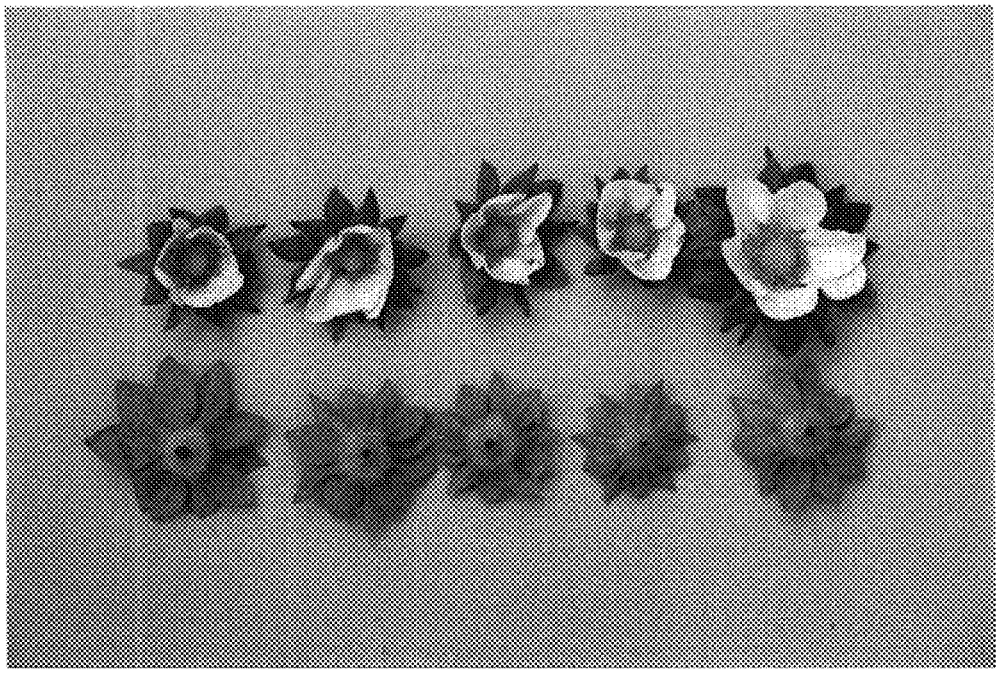
FIG. 3 shows the under side and underside of the flowers.
Figure 4:
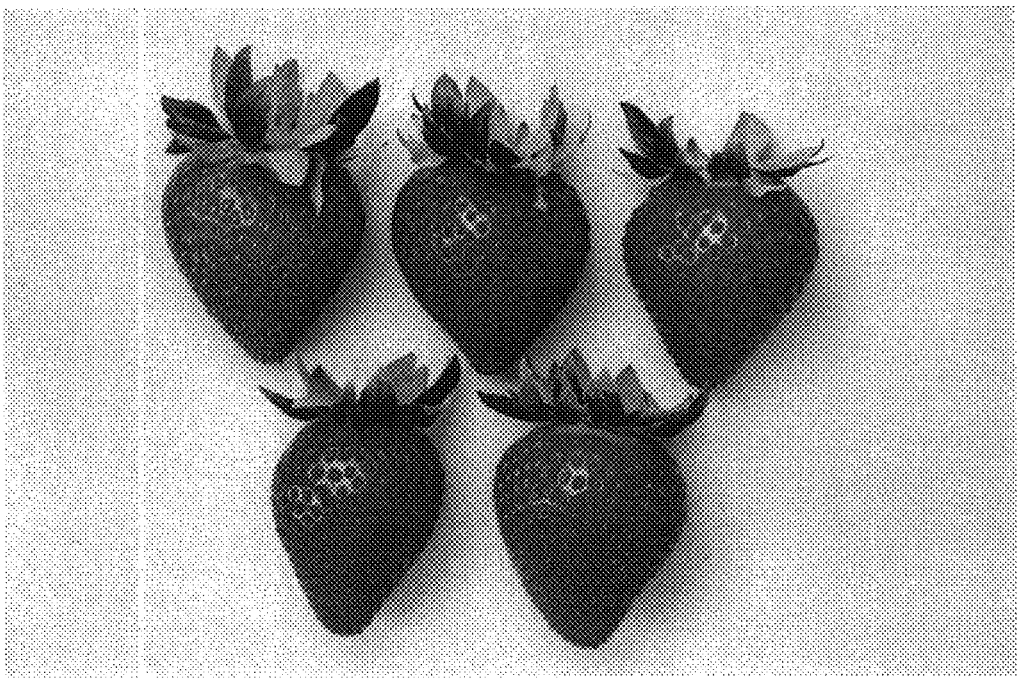
FIG. 4 shows a close-up of the fruit.
Figure 5:
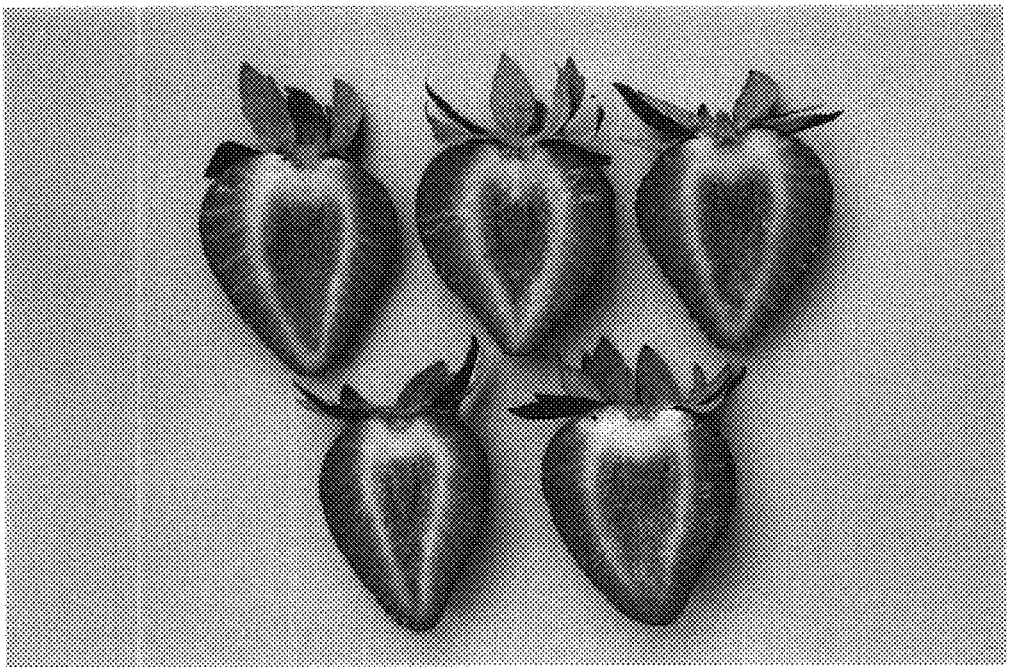
FIG. 5 shows the fruit in longitudinal cross-section.

The following detailed description of the new variety is based upon observations taken of plants harvested from a nursery in McArthur, Calif. in October and held in cold storage until planting in Monterey County, Calif. in November and December of the same year. Plants were grown in raised beds of soil under conditions typical of commercial strawberry production in Monterey County, Calif. Fruits were harvested twice weekly from April, 2003 to November, 2003 for yield determination. Observations of 'Driscoll Pearl', 'San Juan', and 'Driscoll Lanai' were made in side by side comparison in August, 2004. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

6.1 PROPAGATION

The new variety is principally propagated by way of stolons. Although propagation by stolons is presently preferred, other known methods of propagating strawberry plants may be employed.

6.2 CHARACTERISTICS OF THE NEW VARIETY

Information on the new variety is presented in Tables 1, 2, 3 and 4. In the tables, the flowers described are secondary flowers except where indicated. The fruit described is the secondary fruit on eight month old plants. Fruit and flower measurements are an average of both primary and secondary fruit and flowers.

Table 1 provides information on the plant and fruit characteristics of the new variety 'Driscoll Pearl' compared with characteristics of 'San Juan' and 'Driscoll Lanai.' Table 2 provides additional information of the plant and fruit characteristics of the new variety 'Driscoll Pearl' compared with characteristics of the varieties 'San Juan' and 'Driscoll Lanai.' Table 3 provides reactions of the new variety to stresses, pests and diseases compared with reactions of the varieties 'San Juan' and 'Driscoll Lanai.' Table 4 provides isozyme characteristics of the new variety as compared to that of the varieties 'San Juan' and 'Driscoll Lanai.'

TABLE 1

QUANTITATIVE COMPARISON OF 'DRISCOLL PEARL,' 'SAN JUAN' AND 'DRISCOLL LANAI'

| | 'Driscoll Pearl' | 'Driscoll Lanai' | 'San Juan' |
|---|---|---|---|
| Plant Characteristics | | | |
| Height of Plant (cm) | 34.5 | 26.5 | 26.1 |
| Spread of Plant (cm) | 45.7 | 44.7 | 46.6 |
| Number of Crowns | 5.3 | 5.0 | 5.7 |
| Leaf Characteristics | | | |
| Terminal Leaflet Length (cm) | 7.7 | 6.6 | 7.5 |
| Terminal Leaflet Width (cm) | 6.9 | 6.5 | 7.4 |
| Terminal Leaflet Length/Width Ratio | 1.11 | 1.02 | 1.01 |
| # Teeth/Terminal Leaflet | 20.5 | 18.8 | 23.6 |
| Color of upper side | 137B medium green | 139A medium green | 147A medium to dark green |
| Color of under side | 137D light grey green | 138B light green | 147C light green |
| Petiole Length (cm) | 27.4 | 22.5 | 22.7 |
| Petiole Diameter (mm) | 4.1 | 3.6 | 4.2 |
| Petiole Color | 145B yellow green | 145A yellow green | 149A yellow green |
| Petiolule Length (mm) | 18.2 | 14.3 | 10.8 |
| Petiolule Diameter (mm) | 2.2 | 2.5 | 2.1 |
| Petiolule Color | 145C yellow green | 145A yellow green | 149A yellow green |
| Bract Frequency | 8% typically paired | 25% typically single | 75% typically paired |
| Stipule Length (cm) | 3.6 | 3.4 | 3.3 |
| Stipule Width (cm) | 0.6 | 0.7 | 0.6 |
| Stolon Characteristics | | | |
| Anthocyanin color | 59B purple red | 60A purple red | 59A purple red |

TABLE 1-continued

QUANTITATIVE COMPARISON OF 'DRISCOLL PEARL,' 'SAN JUAN' AND 'DRISCOLL LANAI'

| | 'Driscoll Pearl' | 'Driscoll Lanai' | 'San Juan' |
|---|---|---|---|
| Diameter at bract (mm) | 2.56 | 3.16 | 3.19 |
| Avg. # of Daughter plants (2003 Nursery) | 68 | 68 | 67 |
| Flower Characteristics | | | |
| Petal Length (cm) | 1.23 | 0.97 | 1.06 |
| Petal Width (cm) | 1.28 | 1.04 | 1.18 |
| Petal Length/Width Ratio | 0.96 | 0.93 | 0.90 |
| Flower Diameter (cm) | 2.34 | 2.42 | 2.31 |
| Calyx Diameter (cm) | 3.96 | 3.16 | 3.19 |
| Sepal Length (mm) | 15.4 | 11.8 | 11.9 |
| Sepal Width (cm) | 8.7 | 5.9 | 6.9 |
| Petal Color | 155C white | 155C white | 155C white |
| Receptical Color | 154C yellow green | 154C yellow green | 154C yellow green |
| Anther Color | 9A yellow | 9A yellow | 9A yellow |
| Fruiting Truss Length (cm) | 42.8 | 28.8 | 31.2 |
| Fruit Characteristics | | | |
| Fruit Length (cm) | 4.4 | 3.9 | 4.5 |
| Fruit Width (cm) | 3.8 | 4.1 | 4.3 |
| Fruit Length/Width Ratio | 1.15 | 0.96 | 1.03 |
| Average Berry Weight (g) | 24.1 | 23.4 | 25.2 |
| External Color | 53A dark red | 45B orange red | 53A dark red |
| Internal Color | 34B orange red | 47C orange red | 44A red |
| Achene Coloration | 185A to 162A grayed purple to grayed yellow | 185B to 154B grayed purple to grayed yellow | 46B to 16A dark red to yellow |
| Achenes per berry | 318.4 | 323.7 | 330.9 |
| Achene weight (g) | 0.00051 | 0.00049 | 0.00059 |
| 2003 Marketable Yield (g/plant) | 1,854 | 1,679 | 1,499 |

TABLE 2

QUALITATIVE COMPARISON OF 'DRISCOLL PEARL,' 'SAN JUAN' AND 'DRISCOLL LANAI'

| | 'Driscoll Pearl' | 'Driscoll Lanai' | 'San Juan' |
|---|---|---|---|
| Plant | | | |
| Habit | upright | flat | globose to flat globose |
| Canopy Density | open | open | medium |
| Vigor | strong to very strong | medium | medium |
| Leaf | | | |
| Shape in cross section | concave | slightly concave to flat | flat to slightly convex |
| Interveinal blistering | medium | medium | medium to strong |
| Glossiness | weak to medium | weak | weak to medium weak |
| Number of leaflets | three only | three only | sometimes more than 3 leaflets (approx. 17% of leaves) |
| Terminal leaflet margin profile | revolute to flat | revolute to flat | revolute to flat |
| Terminal leaflet shape of base | obtuse to rounded | rounded | obtuse to rounded |

TABLE 2-continued

QUALITATIVE COMPARISON OF 'DRISCOLL PEARL,' 'SAN JUAN' AND 'DRISCOLL LANAI'

| | 'Driscoll Pearl' | 'Driscoll Lanai' | 'San Juan' |
|---|---|---|---|
| Terminal leaflet shape of teeth | rounded | rounded | rounded |
| Stipule pubescence | dense | medium to dense | medium |
| Petiole pubescence | medium to dense | medium | medium |
| Petiole pose of hairs | upwards | downward | outward to downward |
| Stolon | | | |
| Anthocyanin coloration | medium | strong | strong |
| Thickness | thin | medium to thick | medium |
| Pubescence | medium to dense | dense | medium |
| Inflorescence | | | |
| Position relative to foliage | beneath to level with | level to above | beneath to level with |
| Diameter of calyx relative to corolla on secondary flowers | larger | same size to larger | larger |
| Diameter of inner calyx relative to outer on secondary flowers | larger | larger | same size |
| Spacing of petals | overlapping | overlapping | overlapping |
| Fruiting Truss | | | |
| Attitude at first picking | prostrate | prostrate | prostrate |
| Fruit | | | |
| Predominant shape | conical | conical to ovoid | conical to almost cylindrical |
| Difference in shapes between primary and secondary fruits | slight | slight | moderate |
| Band without achenes | very narrow to narrow | narrow to medium | narrow |
| Unevenness of surface | very weak | weak | medium |
| Evenness of color | even | even | even |
| Glossiness | strong | strong | very strong |
| Insertion of achenes | level with surface | level with surface | level with surface |
| Insertion of calyx | level | level | level |
| Pose of the calyx segments | spreading to reflexed | spreading to reflexed | spreading to reflexed |
| Size of calyx in relation to fruit on secondary fruit | smaller | smaller | same size |
| Adherence of calyx | medium to strong | strong | strong |
| Firmness of flesh | medium | medium | firm |
| Evenness of flesh color | slightly uneven | uneven | slightly uneven to even |
| Distribution of flesh color | marginal and central | marginal and central | marginal and central |
| Hollow center size | small to medium | medium | medium |
| Sweetness | strong | medium | medium to strong |
| Texture when tasted | fine | fine | medium |
| Acidity | medium | medium | medium |
| Time of First Flowering in 2003 | early to mid-February | mid-February | mid-February |
| Harvest Interval in 2003 | mid to late-March | late-March to Early November | late-March to Early November |
| Type of Bearing | partially everbearing | partially everbearing | partially everbearing |

6.3 REACTION TO STRESS, PESTS, AND DISEASE

TABLE 3

REACTIONS TO STRESS PESTS AND DISEASES FOR 'DRISCOLL PEARL,' 'SAN JUAN' AND 'DRISCOLL LANAI'

| | 'Driscoll Pearl' | 'Driscoll Lanai' | 'San Juan' |
|---|---|---|---|
| Reaction to Pests | | | |
| *Tetranychus urticae* | moderately susceptible | susceptible | moderately susceptible |
| *Lygus hesperus* | susceptible | susceptible | susceptible |
| Reaction To Diseases | | | |
| Botrytis fruit rot | susceptible | susceptible | susceptible |
| Powdery mildew | highly susceptible | susceptible | susceptible |
| *Verticillium* wilt | moderately resistant | moderately resistant | susceptible |
| Strawberry Mottle Virus | moderately resistant | moderately resistant | moderately resistant |
| *Xanthomonas fragariae* | moderately susceptible | moderately susceptible | moderately susceptible |

6.4 ISOZYME ANALYSIS

In addition to the morphological description above, the new cultivar 'Driscoll Pearl' has been analyzed to obtain an indication of its genetic makeup to provide further means for identifying the new variety and distinguishing it from other somewhat similar and/or related strawberry varieties. Specifically, leaf samples of 'Driscoll Pearl', 'San Juan' and 'Driscoll Lanai' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL PEARL,' 'SAN JUAN' AND 'DRISCOLL LANAI'

| Locus | 'Driscoll Pearl' | 'Driscoll Lanai' | 'San Juan' |
|---|---|---|---|
| PGI | A2 | A1 | A2 |
| LAP | B3 | B3 | B3 |
| PGM | C4 | C2 | C4 |

What is claimed:

1. A new and distinct variety of strawberry plant, substantially as shown and described.

* * * * *